(12) United States Patent
Metzger et al.

(10) Patent No.: US 9,585,758 B2
(45) Date of Patent: Mar. 7, 2017

(54) KNEE PROSTHESIS SYSTEMS AND METHODS

(71) Applicant: Biomet Manufacturing, LLC, Warsaw, IN (US)

(72) Inventors: Robert Metzger, Wakarusa, IN (US); Andrew L. Pierce, Warsaw, IN (US); David R. Brown, Warsaw, IN (US); Brian M. May, Warsaw, IN (US); Joshua R. Porter, Winona Lake, IN (US); Larabeth G. Ryan, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 86 days.

(21) Appl. No.: 13/796,458

(22) Filed: Mar. 12, 2013

(65) Prior Publication Data
US 2014/0277535 A1    Sep. 18, 2014

(51) Int. Cl.
*A61F 2/38*    (2006.01)
*A61F 2/30*    (2006.01)

(52) U.S. Cl.
CPC .......... *A61F 2/3836* (2013.01); *A61F 2/385* (2013.01); *A61F 2/3868* (2013.01); *A61F 2/3886* (2013.01); *A61F 2002/30604* (2013.01); *A61F 2002/30616* (2013.01)

(58) Field of Classification Search
CPC ........................................... A61F 2/38
USPC .................. 623/20.14–20.17, 20.21–20.36
See application file for complete search history.

(56) References Cited

U.S. PATENT DOCUMENTS

| | | | |
|---|---|---|---|
| 4,224,697 | A | 9/1980 | Murray et al. |
| 4,257,129 | A | 3/1981 | Volz |
| 4,673,408 | A | 6/1987 | Grobbelaar |
| 4,938,769 | A | 7/1990 | Shaw |
| 5,330,534 | A | 7/1994 | Herrington et al. |
| 5,358,527 | A | 10/1994 | Forte |

(Continued)

FOREIGN PATENT DOCUMENTS

| | | |
|---|---|---|
| FR | 2780636 A1 | 1/2000 |
| WO | WO-2014159188 A1 | 10/2014 |

OTHER PUBLICATIONS

International Search Report and Written Opinion mailed May 30, 2014 for PCT/US2014/022438 claiming benefit of U.S. Appl. No. 13/796,458, filed Mar. 12, 2013.

(Continued)

*Primary Examiner* — Yashita Sharma
(74) *Attorney, Agent, or Firm* — Schwegman Lundberg & Woessner, P.A.

(57) ABSTRACT

A knee prosthesis system constructed in accordance to one example of the present disclosure can include a femoral component, a tibial component, a first femoral component insert, a second femoral component insert, a first tibial bearing, and a second tibial bearing. The knee prosthesis system may be configured in one of a non-hinged configuration and a second hinged configuration. In the first non-hinged configuration, the first femoral component insert is positioned relative to the femoral component and the first tibial bearing is positioned onto the tibial component. In the second hinged configuration, the second femoral component insert is positioned relative to the femoral component and the second tibial bearing is positioned onto the tibial component.

19 Claims, 5 Drawing Sheets

(56) References Cited

U.S. PATENT DOCUMENTS

| | | | |
|---|---|---|---|
| 5,370,699 | A | 12/1994 | Hood et al. |
| 5,395,401 | A | 3/1995 | Bahler |
| 5,702,464 | A | 12/1997 | Lackey et al. |
| 5,766,257 | A | 6/1998 | Goodman et al. |
| 5,800,552 | A | 9/1998 | Forte |
| 5,824,102 | A | 10/1998 | Buscayret |
| 5,824,103 | A | 10/1998 | Williams |
| 5,871,545 | A | 2/1999 | Goodfellow et al. |
| 6,620,198 | B2 | 9/2003 | Burstein et al. |
| 6,629,999 | B1 | 10/2003 | Serafin, Jr. |
| 6,709,461 | B2 | 3/2004 | O'Neil et al. |
| 6,926,738 | B2 | 8/2005 | Wyss |
| 2008/0004708 | A1* | 1/2008 | Wyss ................... 623/20.24 |
| 2008/0167722 | A1* | 7/2008 | Metzger et al. ........... 623/20.36 |
| 2009/0299482 | A1 | 12/2009 | Metzger et al. |
| 2010/0125339 | A1 | 5/2010 | Earl et al. |
| 2010/0174378 | A1 | 7/2010 | Metzger et al. |
| 2013/0190883 | A1 | 7/2013 | Collard et al. |

OTHER PUBLICATIONS

"International Application Serial No. PCT/US2014/022438, International Preliminary Report on Patentability mailed Sep. 24, 2015", 8 pgs.

* cited by examiner

KNEE PROSTHESIS SYSTEMS AND METHODS

FIELD

The present disclosure relates generally to knee joint prostheses and more particularly, to a knee prosthesis system having a femoral component, a bearing component, a tibial component, and a collection of inserts that may be selectively and alternatively used to convert the femoral component and tibial component for use in at least one of either a non-hinged configuration and a hinged configuration.

BACKGROUND

This section provides background information related to the present disclosure which is not necessarily prior art.

A knee joint prosthesis typically comprises a femoral component, a bearing component, and a tibial component. The femoral component and tibial component are designed to be surgically attached to the distal end of the femur and the proximal end of the tibia, respectively. The femoral component is further designed to cooperate with the bearing in conjuction with the tibial component in simulating the articulating motion of an anatomical knee joint. Such knee joint prostheses are generally referred to as primary knee prostheses.

Knee joint prostheses, in combination with ligaments and muscles, attempt to duplicate natural knee motion as well as absorb and control forces generated during the range of flexion. In some instances however, it may be necessary to replace an existing prosthesis. Such replacement prostheses are generally referred to as revision knee prostheses. Depending on the degree of damage or deterioration of the primary knee prosthesis, knee tendons and ligaments, however, it may be necessary for a revision knee joint prosthesis to eliminate one or more of these motions in order to provide adequate stability. In this way, it may be desirable to provide a fully constrained revision knee, a posterior stabilized (PS) revision knee, or a hinged revision knee for example.

SUMMARY

This section provides a general summary of the disclosure, and is not a comprehensive disclosure of its full scope or all of its features.

A knee prosthesis system constructed in accordance to one example of the present disclosure can include a femoral component, a tibial component, a first femoral component insert, a second femoral component insert, a first tibial bearing, and a second tibial bearing. The knee prosthesis system may be configured in one of a first non-hinged configuration and a second hinged configuration. In the first non-hinged configuration, the first femoral component insert is positioned relative to the femoral component and the first tibial bearing is positioned onto the tibial component. In the second hinged configuration, the second femoral component insert is positioned relative to the femoral component and the second tibial bearing is positioned onto the tibial component.

The femoral component can include a medial and lateral condyle portion connected by a patellar track portion and a femoral box. The femoral box can define a first pair of passages therethrough. The tibial component can have a platform portion and an inferiorly extending stem. The first femoral component insert can have a first pair of closed walls. The first femoral component insert can be sized to selectively locate at the femoral box. The second femoral component insert can have a second pair of walls that define a second pair of passages therethrough. The second femoral component insert can be sized to selectively locate at the femoral box wherein the first and second pair of passages cooperatively align for receipt of an axle. The first tibial bearing can have first bearing surfaces that are configured to engage the medial and lateral condyle portions. The second tibial bearing can have second bearing surfaces that are configured to engage the medial and lateral condyle portions. The second tibial bearing can further comprise a superiorly extending portion defining an axle passage.

According to additional features, the tibial component can further comprise a first interlocking detail configured thereon. The knee prosthesis system can further comprise a first tibial tray insert having a first bearing opposing structure and a second interlocking detail configured thereon. A second tibial tray insert can have a second bearing opposing structure and a third interlocking detail thereon. The first and second tibial tray inserts can be selectively and alternatively coupled to the tibial component. The first bearing engaging structure can be configured to cooperate with the first tibial bearing in a fixed relationship. The second bearing engaging structure can be configured to cooperate with the second tibial bearing in a rotating relationship.

According to still other features, the first interlocking detail can comprise one of a male and female dovetail. The second and third interlocking detail may comprise the other of the male and female dovetail. A fastener can be selectively and alternatively coupled to the first and second femoral component inserts to the femoral component. A locking bar can be configured to selectively couple the first tibial bearing to the first tibial tray insert.

According to other features, the first bearing opposing structure of the first tibial tray insert can comprise a pair of posts that are integrally formed on a superior surface at an anterior edge thereof. A retaining rail can extend from a posterior edge thereof. The locking bar can be configured to selectively engage the pair of posts and the first tibial bearing in the first non-hinged configuration. The second tibial tray insert can include a superiorly extending post configured to be received at the superiorly extending portion of the second tibial bearing in the second hinged configuration.

According to still other features, the knee prosthesis system can further comprise a third tibial tray insert having a fourth interlocking detail configured to selectively mate with the first interlocking detail of the tibial component. The third tibial tray insert can have a body portion sized to oppose substantially all of the platform portion of the tibial component.

A method for implanting a knee prosthesis according to the present disclosure can include providing a knee prosthesis system including a femoral component having a femoral box defining a first pair of passages, a tibial component having a platform, a first femoral component insert having a first pair of closed walls, and a second femoral component insert having a second pair of walls that define a second pair of passages therethrough. One of the first and second femoral component inserts may be intraoperatively removed from the femoral box. The other of the first and second femoral component inserts may be positioned adjacent the femoral box. Removing and positioning the first and second femoral component inserts can convert the knee prosthesis system between a non-hinged configuration and a hinged configuration.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

At the outset, the instant disclosure provides a knee prosthesis system having various knee prostheses that may be adapted for use in a revision knee procedure. Various components are described that may be used alone or as part of a posterior stabilized (PS) knee revision, fully constrained knee revision, and hinged knee revision. As will become more appreciated from the following discussion, the instant disclosure further provides various adapters that may be used in any combination with a tibial and femoral component disclosed herein. Moreover, selection of any of the described components from the knee prosthesis system may be selected intraoperatively by the surgeon performing the procedure.

Figure 1:
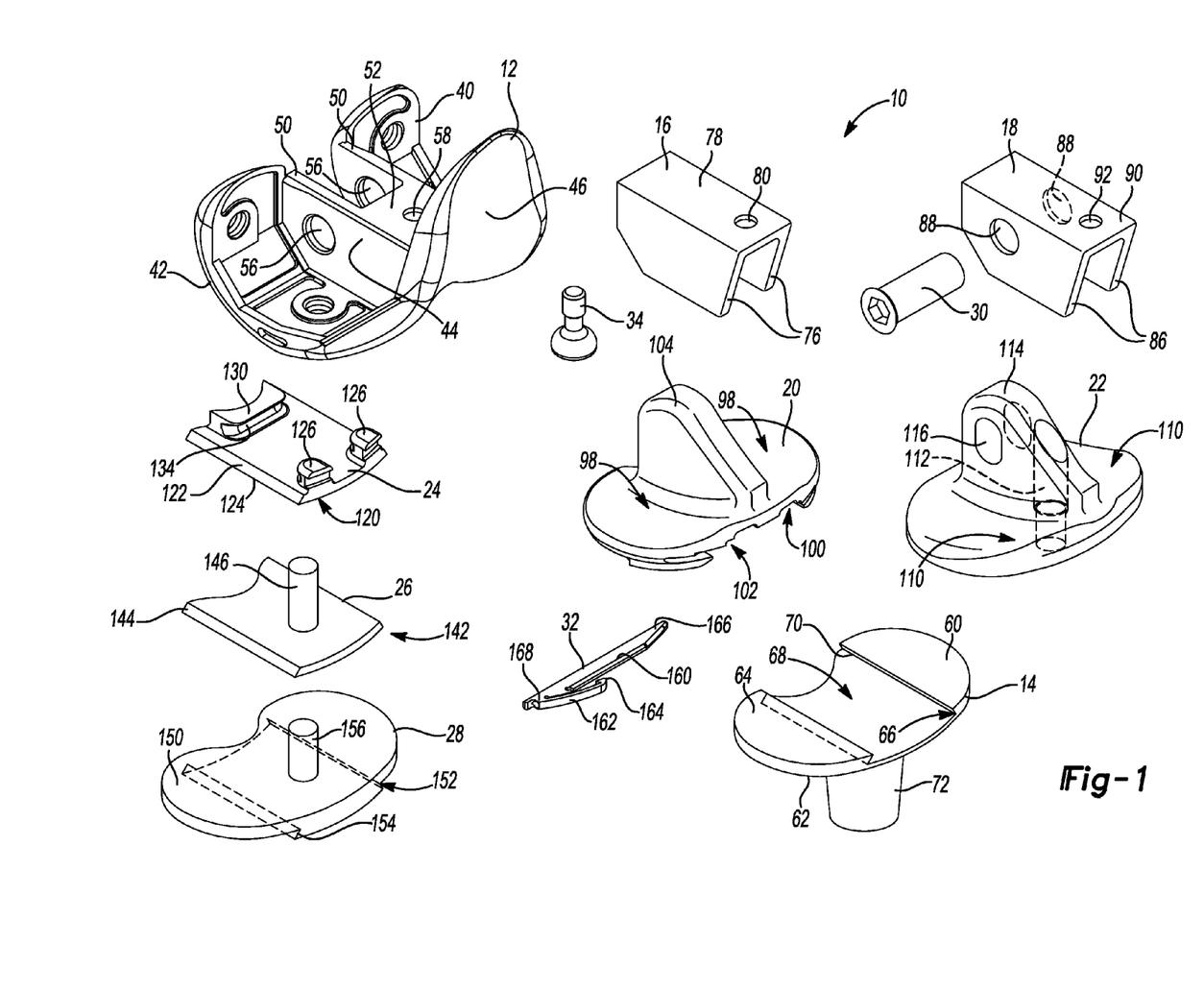
FIG. 1 is a front perspective view of a knee prosthesis system constructed in accordance to one example of the present disclosure.

With initial reference to FIG. 1, a knee prosthesis system constructed in accordance to one example of the present disclosure is shown and generally identified as reference numeral 10. As will become appreciated, the knee prosthesis system 10 can provide various components and adapters that may be intraoperatively exchanged to convert a single femoral component and a single tibial component for use in either a first non-hinged configuration (FIG. 4) or a second hinged configuration (FIG. 6).

The knee prosthesis system 10 can generally include a femoral component 12, a tibial component 14, a first femoral component insert 16, a second femoral component insert 18, a first tibial bearing 20, a second tibial bearing 22, a first tibial tray insert 24, a second tibial tray insert 26, and a third tibial tray insert 28. The knee prosthesis system can further comprise an axle 30, a locking bar 32, and a fastener 34. As will become appreciated herein, the knee prosthesis system 10 allows a surgeon to use a common femoral component 12 and tibial component 14 for applications that require both a non-hinged configuration and a hinged configuration. For example, in a first non-hinged configuration, and as further shown in FIGS. 2-4, a surgeon may use the femoral component 12, the first femoral component insert 16, the fastener 34, the first tibial bearing 20, the tibial component 14, the first tibial tray insert 24, and the locking bar 32. Alternatively, a surgeon may determine that a particular patient will require a more constrained configuration. When a more constrained configuration may be desirable, a surgeon may use the knee prosthesis system 10 to create a hinged configuration.

Figure 5:
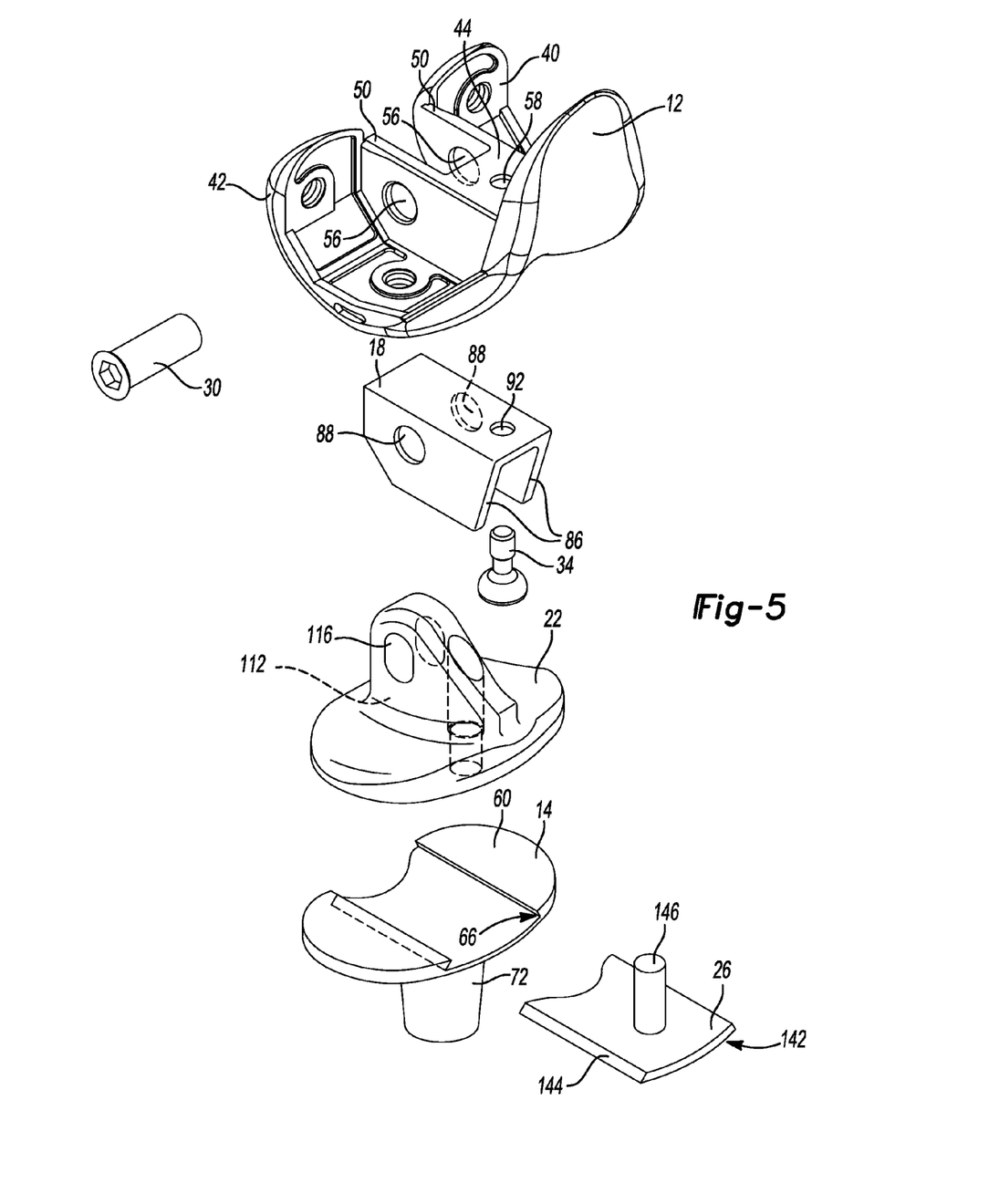
FIG. 5 is an exploded perspective view of various components of the knee prosthesis system of FIG. 1 configured for use in a first hinged configuration.
Figure 6:
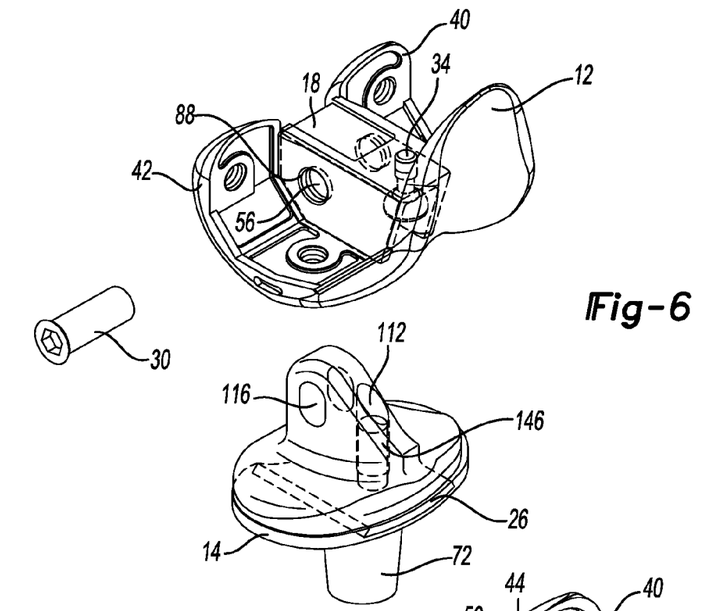
FIG. 6 is a partial exploded view of the components of FIG. 5 and shown with a second femoral component insert coupled to the femoral component according to one example.
Figure 7:
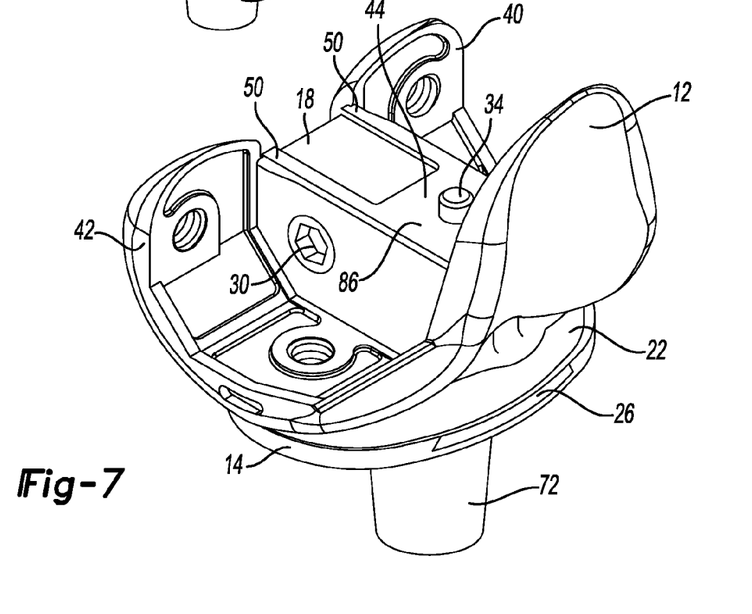
FIG. 7 is a front perspective view of the knee prosthesis components shown in FIG. 5 in an assembled, hinged configuration.

In a hinged configuration, and as further shown in FIGS. 5-7, a surgeon may use the femoral component 12, the second femoral component insert 18, the axle 30, the fastener 34, the second tibial bearing 22, the tibial component 14, and the second tibial tray insert 26. In one advantage of the knee prosthesis system 10 according to the present disclosure, a surgeon may intraoperatively exchange components to convert the prosthesis between a hinged and a non-hinged configuration without disturbing the femoral component 12 and the tibial component 14. In this way, it is contemplated that in one example, a surgeon may have implanted the knee prosthesis system 10 in a non-hinged configuration and, over time, the knee joint of the patient may deteriorate. In such an example, a surgeon may surgically access the implanted non-hinged knee prosthesis and exchange the first femoral component insert 16 for a second femoral component insert 18, the first tibial bearing 20 for the second tibial bearing 22, and the first tibial tray insert 24 with the second tibial tray insert 26. The axle 30 may be used to hingedly couple the femoral component 12 to the second tibial bearing 22. As described herein, the first tibial bearing 20 is a fixed bearing whereas the second tibial bearing 22 is a rotating bearing.

Returning now to FIG. 1, the femoral component 12 will be described in greater detail. The femoral component 12 can generally comprise a medial condyle portion 40 and a lateral condyle portion 42. The condyle portions 40 and 42 can replace the medial and lateral condyles of a distal femur. The medial and lateral condyle portions 40 and 42 can interconnect through a femoral box 44 and a patellar track portion 46. The femoral box 44 can generally comprise a pair of generally parallel walls 50 that connect through a connecting wall 52. The walls 50 define a first pair of passages 56 therethrough. The connecting wall 52 can define a bore 58. It will be appreciated that the femoral component 12 may comprise other features and/or be configured differently without departing from the scope of the present disclosure.

The tibial component 14 can generally include a platform portion 60 having an inferior bone engaging surface 62 and a superior bearing opposing surface 64. The platform portion 60 can further provide a first interlocking detail 66 on the superior bearing opposing surface 64. In one example, the first interlocking detail 66 can provide a slot 68 having a female dovetail 70. A tibial stem 72 can extend generally inferiorly from the tibial component 14.

The first femoral component insert 16 can generally have a first pair of closed walls 76 that are connected by a transverse wall 78. A hole 80 may be formed through the transverse wall 78. In general, the first femoral component insert 16 can be dimensioned so as to fit between the walls 50 on the femoral box 44 of the femoral component 12 (see FIG. 4). The second femoral component insert 18 can generally comprise a pair of lateral walls 86 that define second passages 88 therethrough. A transverse wall 90 generally connects the walls 86. A hole 92 may be formed through the transverse wall 90. As with the first femoral component insert 16 described above, the second femoral component insert 18 may be dimensioned so as to fit between the walls 50 of the femoral box 44 on the femoral component 12 (see FIG. 6).

The first tibial bearing 20 can include first bearing surfaces 98 configured to engage the medial and lateral condyle portions 40 and 42 of the femoral component 12. The first tibial bearing 20 can further comprise engaging structure 100 formed on an inferior side 102 thereof. A superiorly extending portion 104 may be formed on the first tibial bearing 20. The first tibial bearing 20 can be formed of ultra-high molecular weight polyethylene (UHMWPE).

The second tibial bearing 22 can generally include first bearing surfaces 110 configured to engage the medial and lateral condyle portions 40 and 42 of the femoral component 12. The second tibial bearing 22 can further include a post bore 112 defined therein. A superiorly extending portion 114 can define an axle passage 116 therethrough. The second tibial bearing 22 can additionally include structure that interfaces with the inserts 26 and 28 and/or the tibial component 14 to inhibit liftoff. The second tibial bearing 22 can be formed from a surgical grade, low-friction, and low-wearing plastic, such as UHMWPE or other suitable material. Other tibial bearing configurations may also be employed. For example, the bearings can be linked or non-linked. Additionally, fixed and rotating platform bearings may also be used. In still other examples, a one-piece tibial tray can incorporate various bearings to go between non-linked and linked. Such examples may be found in Applicants' co-pending owned U.S. patent application Ser. No. 13/796,440, filed Mar. 12, 2013, entitled KNEE JOINT PROSTHESIS SYSTEM AND METHOD FOR IMPLANTATION, which is filed concurrently herewith and incorporated by reference in its entirety.

The first tibial tray insert 24 can generally include a first bearing opposing structure 120 and a second interlocking detail 122. In the example shown, the second interlocking detail 122 is in the form of a male dovetail 124. The first tibial tray insert 24 can further comprise a pair of posts 126 integrally formed on a superior surface at an anterior edge thereof. A retaining rail 130 may extend from a posterior edge thereof. As will be described herein, the posts 126 and retaining rail 130 may cooperate with the locking bar 32 to engage and couple with the engaging structure 100 on the first tibial bearing 20. The retaining rail 130 can define a retaining slot 134. The second tibial tray insert 26 can include a second interlocking detail 142 in the form of a male dovetail 144. The second tibial tray insert 26 can further comprise a post 146 extending superiorly therefrom. The third tibial tray insert 28 may be formed similarly to the second tibial tray insert 26. However, the third tibial tray insert 28 may include a body portion 150 that can generally extend substantially across the profile of the platform portion 60 of the tibial component 14. The third tibial tray insert 28 can include a third interlocking detail 152 in the form of a male dovetail 154. The third tibial tray insert 28 can further comprise a post 156 extending superiorly therefrom.

The locking bar 32 can generally include a body 160 having a finger 162 extending therefrom. A catch 164 can be formed on a terminal end of the finger 162. The body 160 can further include a leading end 166 and a trailing end 168. The locking bar 32 can be formed of biocompatible metallic material, such as titanium for example.

Figure 2:
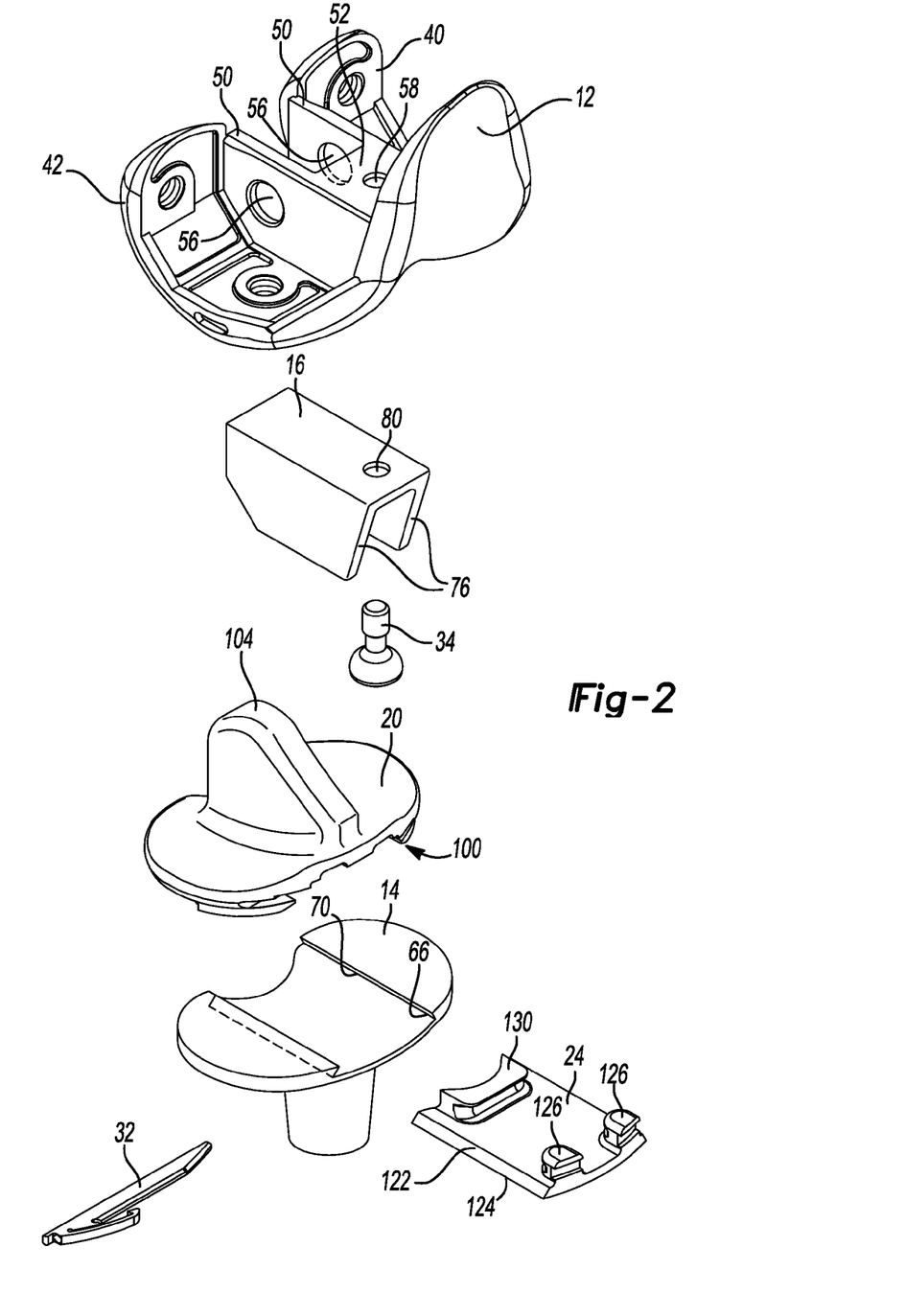
FIG. 2 is an exploded view of various components of the knee prosthesis system of FIG. 1 configured for use in a first non-hinged configuration.
Figures 3, 4:
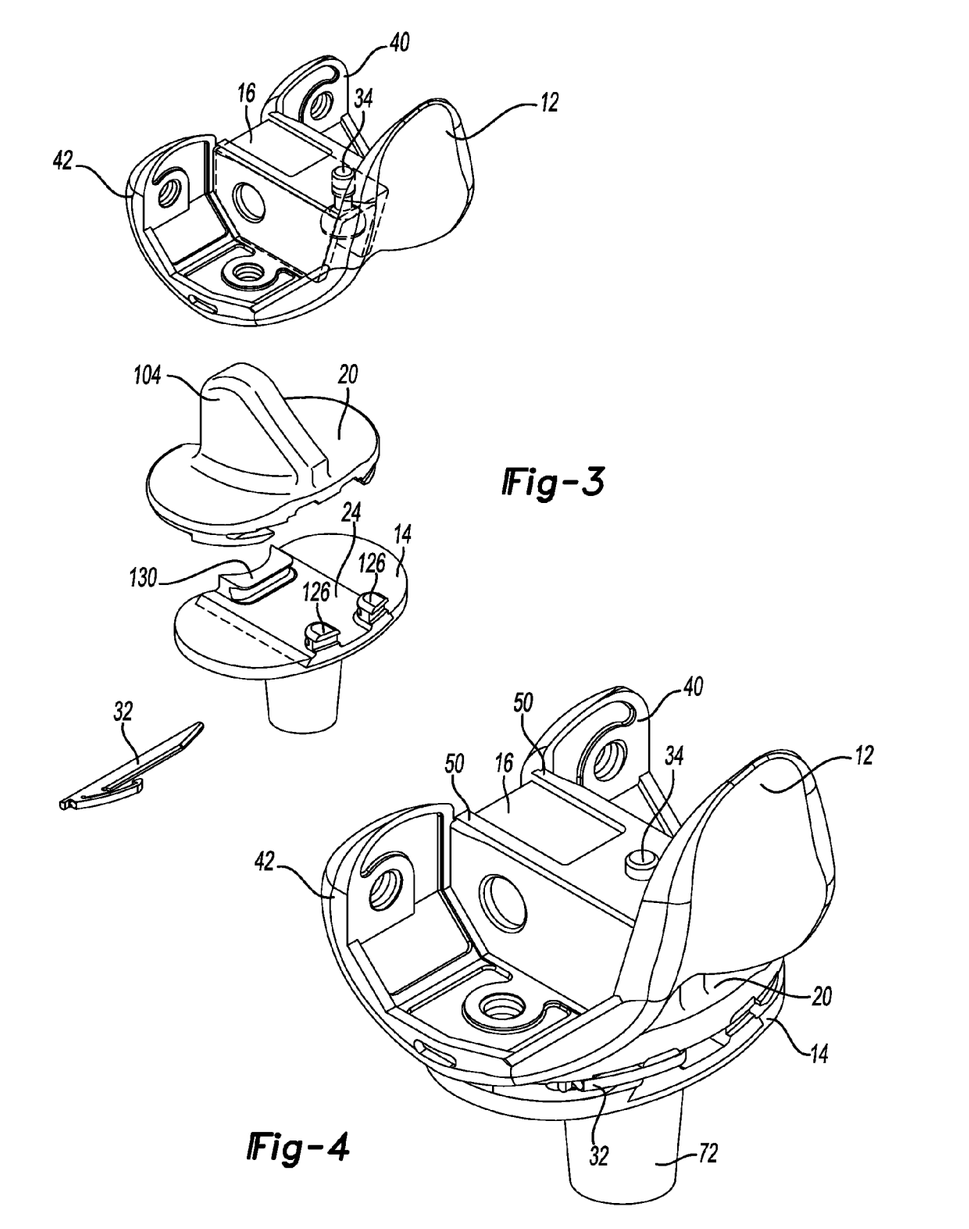
FIG. 3 is a partial exploded view of the components shown in FIG. 2 and illustrating a first femoral component insert coupled to the femoral component according to one configuration.
FIG. 4 is a front perspective view of the components shown in FIG. 2 in an assembled, non-hinged configuration.

With particular reference now to FIGS. 2-4, a method for assembling the knee prosthesis system 10 in a first non-hinged configuration will be described. The first femoral component insert 16 may be generally located between the walls 50 of the femoral box 44 on the femoral component 12. In this regard, the closed walls 76 can act to close the first passages 56 on the femoral component 12. The fastener 34 may be advanced through the hole 80 in the first femoral component insert 16 and coupled to the connecting wall 52 such as at threads formed on the bore 58. In an example, the first femoral component insert 16 can be held in a fixed relationship relative to the femoral component 12, such as via the fastener 34. In another example, the first femoral component insert 16 can be optional.

The first tibial tray insert 24 can be slidably coupled to the tibial component 14. In one example, the second interlocking detail 122 can be advanced along the first interlocking detail 66 on the tibial component 14. In this regard, the female dovetail 70 on the tibial component 14 can lockingly couple with the corresponding male dovetail 124 on the first tibial tray insert 24. The first tibial bearing 20 can then be located onto the first tibial tray insert 24 and tibial component 14. The engaging structure 100 of the first tibial bearing 20 can cooperatively align with the respective posts 126 and retaining rail 130. The locking bar 32 can then be advanced between the engaging structure 100 of the first tibial bearing 20 and the posts 126 on the first tibial tray insert 24. A more detailed discussion of how the locking bar 32 cooperates with the posts 126 and corresponding bearing may be found in commonly owned U.S. Pat. No. 5,330,534 entitled "Knee Joint Prosthesis With Interchangeable Components", which is hereby incorporated by reference. In other examples, the tibial component 14 and the first tibial bearing 20 can be integrally formed. An example of how the tibial component 14 and the first tibial bearing 20 can be formed can be found in the Vanguard® Mono-Lock™ Tibial System by Biomet.

Turning now to FIGS. 5-7, a method for assembling the knee prosthesis system 10 in a second hinged configuration will be described in greater detail. It will be appreciated that in some examples, the corresponding components required for the non-hinged configuration are first removed from cooperation with the femoral component 12 and the tibial component 14. The second femoral component insert 18 can be located between the walls 50 on the femoral component 12. The second femoral component insert 18 can be positioned such that the second passages 88 align with the first passages 56 on the femoral box 44. The fastener 34 can also be advanced through the hole 92 and the bore 58 to couple the second femoral component insert 18 to the femoral component 12. In an example, the second femoral component insert 18 can be held in a fixed relationship relative to the femoral component 12, such as via the fastener 34. In another example, the second femoral component insert 18 can be optional. In some examples, the fastener 34 can act as a superiorly extending stem. Additionally or alternatively, a separate stem can be incorporated. While a fastener 34 is shown coupling the first and second femoral component inserts 16 and 18, other attachment methods may be employed. In yet other examples, the femoral box 44 can be formed without the passages 56. The axle 30 can be retained entirely within the second femoral component insert 18.

The second interlocking detail 142 of the second tibial tray insert 26 can be slidably advanced into engagement with the first interlocking detail 66 on the tibial component 14. Specifically, the female dovetail 70 on the tibial component 14 can receive the male dovetail 144 on the second tibial tray insert 26. It will be appreciated that while the dovetails 70 and 144 (and others disclosed herein) are shown extending along an anterior/posterior direction, they may extend along other directions such as medial/lateral or superior/inferior. In other examples, the dovetails disclosed herein can be replaced with other structures including slots, various diameters, locking bars, etc. The second tibial bearing 22 can then be located relative to the second tibial tray insert 26. In one example, the post bore 112 can receive the post 146. The axle 30 can then be advanced through all of the first passages 56 on the femoral box 44 of the femoral component 12, the second passages 88 on the second femoral component insert 18, and the axle passage 116 of the second tibial bearing 22.

In other examples, it may be desirable to implant a femoral component having a stem. For example, in instances where a posterior stabilized implant is implanted, an insert (such as the first femoral insert 16) can be removed to expose the femoral canal. The femur can be prepared for receipt of a stem between the condyles. A stemmed femoral insert (or other structure) can then be installed on the femoral component and implanted.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A method for implanting a knee prosthesis, the method comprising:
    providing a knee prosthesis system including a femoral component having a femoral box defining a first pair of passages, a tibial component having a platform, a first femoral component insert having a first pair of closed walls, a second femoral component insert having a second pair of walls that define a second pair of passages therethrough, wherein each of the first femoral component insert and the second femoral component insert comprises a body configured to engage the tibial component within the femoral box:
    intraoperatively removing one of the first and second femoral component inserts from being secured adjacent the femoral box; and
    positioning and securing the other of the first and second femoral component inserts adjacent the femoral box; wherein the removing and positioning converts the knee prosthesis system between a non-hinged configuration and a hinged configuration.

2. The method of claim 1 further comprising:
    providing a first tibial bearing configured for use in a first non-hinged configuration and a second tibial bearing configured for use in a second hinged configuration;
    intraoperatively removing one of the first and second tibial bearings from the tibial component; and positioning the other of the first and second tibial bearings onto the tibial component; wherein removing and positioning the first and second tibial bearings converts the knee prosthesis system between a non-hinged configuration and a hinged configuration.

3. The method of claim 2 wherein the tibial component comprises a first interlocking detail and wherein the method further comprises:
providing a first tibial tray insert having a first bearing opposing structure and a second interlocking detail;
providing a second tibial tray insert having a second bearing opposing structure and a third interlocking detail;
intraoperatively removing one of the first and second tibial tray inserts from interlocking engagement with the first interlocking detail on the tibial component; and
positioning the other of the first and second tibial tray inserts into interlocking engagement with the first interlocking detail on the tibial component thereby converting the tibial tray between the non-hinged configuration and the hinged configuration.

4. The method of claim 3 wherein removing one of the first and second tibial tray inserts comprises slidably translating the one of the first and second tibial tray inserts along a dovetail slot defined on the platform of the tibial component.

5. The method of claim 2, further comprising:
passing an axle through the first and second pairs of passages in the respective femoral component and first femoral component insert in the hinged configuration.

6. The method of claim 5, further comprising:
passing the axle through an axle passage defined through a superiorly extending portion on the second tibial bearing.

7. The method of claim 2, further comprising:
threadably advancing a fastener through a hole defined in one of the first and second femoral component inserts and a cooperatively aligned hole in the femoral box.

8. The method of claim 3, further comprising:
slidably advancing a locking bar into engagement with the first tibial bearing and the first tibial tray insert.

9. The method of claim 1 wherein positioning the other of the first and second femoral component inserts comprises positioning the other of the first and second femoral component inserts between opposing walls on the femoral component that define the femoral box.

10. The method of claim 3 further comprising locating a superiorly extending post on the second tibial tray insert into a corresponding post bore defined in the second tibial bearing.

11. A method for implanting a knee prosthesis, the method comprising:
intraoperatively removing one of a first femoral component insert and a second femoral component insert from being secured in a fixed relationship within a femoral box of a femoral component, the femoral box defining a first pair of passages, and the second femoral component insert defining a second pair of passages;
positioning and securing in a fixed relationship the other of the first femoral component insert and the second femoral component insert adjacent the femoral box;
wherein the removing and the positioning and securing converts the femoral component between a non-hinged configuration and a hinged configuration;
providing a first tibial bearing configured for use in a first non-hinged configuration and a second tibial bearing configured for use in a second hinged configuration;
intraoperatively removing one of the first or the second tibial bearings from a tibial component; and
positioning the other of the first or second tibial bearings onto the tibial component;
wherein removing and positioning the first and the second tibial bearings converts the tibial component between a non-hinged configuration and a hinged configuration.

12. The method of claim 11, further comprising passing a circular axle through the first and the second pairs of passages in the hinged configuration, the first and second pairs of passages forming a circular axle passage such that the second tibial bearing is attached to the femoral component at a fixed location.

13. The method of claim 12, further comprising passing the axle through an oval axle passage defined through a superiorly extending portion on a tibial bearing.

14. The method of claim 12, further comprising advancing a fastener through a hole defined in one of the first and the second femoral component inserts and a cooperatively aligned hole in the femoral box to achieve the fixed relationship.

15. A method for implanting a knee prosthesis, the method comprising:
intraoperatively removing one of a first femoral component insert and a second femoral component insert from being coupled to a femoral box of a femoral component, the femoral box being configured to receive a superiorly extending portion of a tibial component, the femoral box defining a first pair of passages and the second femoral component insert defining a second pair of passages, wherein the first femoral component insert and the second femoral component insert are configured to be positioned between the femoral box and the superiorly extending portion; and
positioning and coupling the other of the first femoral component insert and the second femoral component insert to the femoral box; wherein the removing and the positioning and coupling converts the knee prosthesis system between a non-hinged configuration and a hinged configuration.

16. The method of claim 15, wherein the positioning and coupling of the other of the first or the second femoral component inserts includes positioning the other of the first or the second femoral components inserts between opposing walls on the femoral component that define the femoral box.

17. The method of claim 15, further comprising passing an axle through the first and the second pairs of passages in the hinged configuration.

18. The method of claim 15, wherein the positioning and coupling further comprises advancing a fastener through a hole defined in one of the first or second femoral component inserts and a cooperatively aligned hole in the femoral box.

19. The method of claim 15, wherein each of the first femoral component insert and the second femoral component insert comprises:
a first lateral wall;
a second lateral wall;
a transverse wall connected to the first and second lateral walls; and
a hole passing through the transverse wall.

* * * * *